United States Patent
Bloms-Funke et al.

(10) Patent No.: US 8,084,497 B2
(45) Date of Patent: Dec. 27, 2011

(54) C-(2-PHENYL-CYCLOHEXYL)-METHYLAMINE COMPOUNDS FOR THERAPY OF FIBROMYALGIA

(75) Inventors: Petra Bloms-Funke, Wuerselen (DE); Werner Englberger, Stolberg (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 12/558,896

(22) Filed: Sep. 14, 2009

(65) Prior Publication Data
US 2010/0004341 A1 Jan. 7, 2010

Related U.S. Application Data

(60) Division of application No. 11/440,005, filed on May 25, 2006, now abandoned, which is a continuation of application No. PCT/EP2004/013439, filed on Nov. 26, 2004.

(30) Foreign Application Priority Data

Nov. 28, 2003 (DE) .................................. 103 56 362

(51) Int. Cl.
*A01N 41/02* (2006.01)
*A01N 33/00* (2006.01)
(52) U.S. Cl. ........................................ 514/517; 514/579
(58) Field of Classification Search .................. 514/517, 514/579
See application file for complete search history.

(56) References Cited

U.S. PATENT DOCUMENTS 5,733,936 A * 3/1998 Buschmann et al. ......... 514/646

FOREIGN PATENT DOCUMENTS

| DE | 195 25 137 A1 | 1/1997 |
|---|---|---|
| DE | 102 54 785 A1 | 6/2004 |
| WO | WO 02/43712 A2 | 6/2002 |
| WO | WO 02/067651 A2 | 9/2002 |
| WO | WO 2004/009067 A1 | 1/2004 |
| WO | WO 2004/047823 A1 | 6/2004 |
| WO | WO 2006/094961 A1 | 9/2006 |
| WO | WO 2007/031326 A2 | 3/2007 |

OTHER PUBLICATIONS

Lavin et al. "Use of the Leeds Assessment of Neuropathic Symptoms and Signs Questionnaire in Patients with Fibromyalgia" Seminars in Arthritis and Rheumatism, vol. 32, No. 6 Jun. 2003: pp. 407-411.*
Rao et al. "Pharmacological therapies in fibromyalgia" Best Practice & Research Clinical Rheumatology vol. 17, No. 4, pp. 611-627, 2003.*
Corresponding European Search Report dated Mar. 6, 2009 with English translation (Six (6) pages).
Flick et al., "Untersuchungen Zur Chemischen Struktur und Analgetischen Wirkung Von Phenylsubstituierten Aminomethylcyclohexanolen" (Studies on Chemical Structure and Analgetic Activity of Phenyl Substituted Aminomethycyclohexanoles), Arzneimittel Forschung. Drug Research, Editio Cantor. Aulendorf, DE, BD. 28, NR. 1A, 1978, pp. 107-113, XP000608150.
Leventhal: "Management of Fibromyalgia", Annals of Internal Medicine Dec. 7, 1999, vol. 131, Nr. 11, 1999, pp. 850-858, XP002517722.
Bamigrade et al., "Actions of Tramadol, its Enantiomers and Principal Metabolite, O-desmethyltramadol, on Serotonin (5-HT) Efflux and Uptake in the Rat Dorsal Raphe Nucleus", British Journal of Anasthesia 1997; 79: pp. 352-356.
Halfpenny et al., "Effects of Tramadol Stereolsomers on Norepinephrine Efflux and Uptake in the Rat Locus Coeruleus Measured by Real Time Voltammetry", British Journal of Angesthesis, 1999, pp. 908-915.
Rojas-Corrales et al., "Tramadolinduces Antidepressant-Type Effects in Mice", Elsevier Science Life Sciences, vol. 63, No. 12, pp. 175-180, 1998, Elsevier Science, Inc.

* cited by examiner

*Primary Examiner* — Sreeni Padmanabhan
*Assistant Examiner* — Renee Claytor
(74) *Attorney, Agent, or Firm* — Crowell & Moring LLP

(57) ABSTRACT

Pharmaceutical formulations of [2-(3-methoxyphenyl)-cyclohexylmethyl]-dimethylamine and the metabolites thereof suitable for treating fibromyalgia or chronic pain due to fibromyalgia, and related methods of treating fibromyalgia or chronic pain due to fibromyalgia are described.

9 Claims, No Drawings

C-(2-PHENYL-CYCLOHEXYL)-METHYLAMINE COMPOUNDS FOR THERAPY OF FIBROMYALGIA

CROSS-REFERENCE TO RELATED APPLICATIONS

This application is a division of co-pending application Ser. No. 11/440,005, filed May 25, 2006, which in turn was is a continuation of International patent application Ser. No. PCT/EP2004/013439 filed Nov. 26, 2004, which claims priority from Federal Republic of Germany patent application no. DE 103 56 362.8 filed Nov. 28, 2003, the disclosures of which are incorporated herein in their entireties.

FIELD OF THE INVENTION

Pharmaceutical formulations of [2-(3-methoxyphenyl)-cyclohexylmethyl]-dimethylamine and the metabolites thereof for treating anxiety, anxiety attacks and disorders as well as depression. Related methods of treating anxiety and anxiety attacks or depression are also provided, including methods of administering the active compound(s) as adjuvant(s) to at least one antidepressant.

BACKGROUND OF THE INVENTION

Anxiety disorders are illnesses of which the main symptoms are manifestations of unrealistic or excessively pronounced anxiety. In the case of phobias, to the sub-types of which so-called simple phobias, social anxiety disorders and agoraphobias belong, the anxiety attacks are associated with particular objects or situations. However, pronounced anxiety attacks can also occur without being triggered by specific situations or circumstances. Thus panic disorders are distinguished by recurring, pronounced anxiety attacks which are not foreseeable and therefore lead to anticipatory anxiety. Generalized anxiety disorders are floating, lasting anxieties with diverse, in particular vegetative symptoms. Patients who suffer from posttraumatic stress disorders (PTSD) were exposed to a brief or long-lasting event or occurrence of exceptional threat or with catastrophic proportions. This event would induce a deep-seated despair in virtually anyone. Those affected live through the stresses again and again in quick-fire images, accompanied by psychovegetative symptoms, such as, inter alia, severe outbreaks of perspiration and a racing heart. Obsessive compulsive disorders (OCD) are characterized by recurring unpleasant thoughts, impulses or actions which last several weeks, are experienced as being part of the self and against which at least partial resistance is given since the person affected finds them senseless. Mixed anxiety disorders or anxiety disorders accompanied with depressions very often exist.

Depressions are affectivity disorders in which a depressive syndrome is of prime significance, depressive meaning associated with depression or of sad mood. The depressive illnesses include unipolar severe depressions with or without delusion, moderate depressions, mild depressions, dysthymia, melancholy, bipolar depressions (bipolar illness I, mania and severe depression; bipolar illness II, hypomania and severe depressions; cyclothymic personality disorders, hypomania and mild depressions).

Those pharmaceutical formulations with an anxiolytic and antidepressant action based on an inhibition of the reuptake of the monoamines noradrenaline and/or serotonin are widely used for therapy of anxiety disorders and depressions (Pacher, P., Kohegyi, E., Kecskemeti, V., Furst, S., Current Medicinal Chemistry 2001, 8, 89-100; Goddard, A. W., Coplan, J. D. Gorman, J. M., Charney, D. S., in: Neurobiology of mental illness, Charney, D. S., Nestler, E. J., Bunney, B. S. (eds.), Oxford University Press, New York, 1999, p. 548-563). A great disadvantage in this context is that the monoamine reuptake inhibitors display their anxiolytic and antidepressant action only after several weeks of treatment and achieve their full activity only after approx. 3-4 weeks. At the start of treatment of patients suffering from anxiety, and also those suffering from depression, standard medications frequently intensify or induce anxiety states, unrest, increased irritability and thoughts of suicide. These psychomotor states of excitation and thoughts of suicide occur particularly frequently in the first days after the start of therapy both with tricyclic antidepressants, selective serotonin reuptake inhibitors (so-called SSRIs) and with mixed serotonin-noradrenalin reuptake inhibitors, and are associated with an increased risk of suicide (Jick, H., Kaye, J. A., Jick, S. S.: Antidepressants and the risk of suicidal behaviours, JAMA (2004) 292, 338-343). This results in the need for strict monitoring of patients being treated with standard antidepressants, and possibly for a reduction in the dose. For anxiety disorders and depressions there is therefore a great need for a therapy which is distinguished by an early onset of action and causes no anxiogenic side effects and therefore no increased risk of suicide at the start of therapy, or inhibits those induced by antidepressants.

Since approx. 20-30% of patients suffering from anxiety disorders and depressions show no improvement after treatment with approved antidepressants and anxiolytics, new therapeutic systems for treatment of hitherto pharmacotherapy-resistant patients are of high benefit.

The monoamine reuptake inhibitors used for therapy of anxiety disorders and depressions are also used for treatment of chronic pain patients. In addition to the actual antidepressant and anxiolytic actions, reuptake inhibitors of noradrenaline and serotonin lead to an independent analgesic action in that descending pain inhibition pathways at the level of the spinal marrow are activated. Monoamine reuptake inhibitors are employed clinically for monotherapy of neuropathic pain, and also as an adjuvant to opiates for treatment of chronic pain (inter alia inflammatory pain, tumour pain, fibromyalgia) (Sindrup, in: Yaksh, T. L., et al., Anesthesia. Biological foundations. Philadelphia: Lippincott-Raven, 1997, 987-997). Since chronic pain is accompanied by anxiety disorders or depressions in a large number of patients, a substance with µ-opiate agonistic properties combined with a clinically relevant serotonin and/or noradrenaline reuptake inhibition is particularly favourable.

SUMMARY OF THE INVENTION

One object of the present invention is to provide substances, in particular opioid substance, which are suitable for therapy of anxiety disorders, depressions or mixed forms of anxiety and depression with or without chronic pain. In particular, the invention provides compounds with an earlier onset of action compared with the monoamine reuptake inhibitors widely used for anxiety disorders and depressions.

It has now been found, surprisingly, that 2-(3-methoxyphenyl)-cyclohexylmethyl)-dimethylamine and also its metabolites, and in this context in particular 3-(2-dimethylaminomethyl-cyclohexyl)-phenol, have a therapeutically relevant anxiolytic and antidepressant action component which is distinguished by an early onset of action and the absence of anxiogenic effects. Mechanistic investigations show the content of the µ-opiate agonistic component in the anxiolytic as well as in the antidepressant action and in particular in the early onset of action. The substances have pronounced anxiolytic, antidepressant and analgesic actions and are therefore suitable for treatment of depressions, anxiety disorders and pain. On the basis of the μ-opiate agonistic action component, of the anxiolytic and antidepressant actions mediated by serotonin and noradrenaline reuptake inhibition, the use according to the invention of the compounds mentioned is a particularly effective treatment possibility precisely also for pharmaco-resistant anxiety and depression patients.

The invention accordingly provides the use of
3-(2-dimethylaminomethyl-cyclohexyl)-phenol,
(1R,2R)-3-(2-dimethylaminomethyl-cyclohexyl)-phenol,
[2-(3-methoxyphenyl)-cyclohexylmethyl]-dimethylamine,
(1R,2R)-[2-(3-methoxyphenyl)-cyclohexylmethyl]-dimethylamine,
sulfuric acid mono-[3-(2-dimethylaminomethyl-cyclohexyl)-phenyl]ester,
sulfuric acid mono-(1R,2R)-[3-(2-dimethylaminomethyl-cyclohexyl)-phenyl]ester,
3-(2-methylaminomethyl-cyclohexyl)-phenol,
(1R,2R)-3-(2-methylaminomethyl-cyclohexyl)-phenol,
3-(2-dimethylaminomethyl-cyclohexyl)-phenol, N-oxide,
(1R,2R)-3-(2-dimethylaminomethyl-cyclohexyl)-phenol, N-oxide,
6-[3-(2-dimethylaminomethyl-cyclohexyl)-phenoxy]-3,4,5-trihydroxy-tetrahydropyran-2-carboxylic acid,
6-[(1R,2R)-3-(2-dimethylaminomethyl-cyclohexyl)-phenoxy]-3,4,5-trihydroxy-tetrahydropyran-2-carboxylic acid,
4-(2-dimethylaminomethyl-cyclohexyl)-catechol,
(1R,2R)-4-(2-dimethylaminomethyl-cyclohexyl)-catechol,
3-(2-aminominome-cyclohexyl)-phenol,
(1R,2R)-3-(2-aminomethyl-cyclohexyl)-phenol,
C-[2-(3-methoxy-phenyl)-cyclohexyl]-methylamine,
(1R,2R)-C-[2-(3-methoxy-phenyl)-cyclohexyl]-methylamine,
[2-(3-methoxy-phenyl)-cyclohexylmethyl]-methylamine,
(1R,2R)-[2-(3-methoxy-phenyl)-cyclohexylmethyl]-methylamine,
[2-(3-methoxy-phenyl)-cyclohexylmethyl]-dimethylamine, N-oxide or
(1R,2R)-[2-(3-methoxy-phenyl)-cyclohexylmethyl]-dimethylamine, N-oxide,
optionally in the form of their racemates, their pure stereoisomers, in particular enantiomers or diastereomers, or in the form of mixtures of the stereoisomers, in particular the enantiomers or diastereomers, in any desired mixture ratio; in the form shown or in the form of their acids or their bases or in the form of their salts, in particular the physiologically acceptable salts, or in the form of their solvates, in particular the hydrates;

for the preparation of a pharmaceutical formulation for treatment of anxiety states or for the preparation of an adjuvant to standard antidepressants as well as for related methods of treatment.

It is particularly preferable in this context if the compounds used are in the form of 1R,2R enantiomers.

The term salt is to be understood as meaning any form of the active compound according to the invention in which this assumes an ionic form or is charged and is coupled with a counter-ion (a cation or anion) or is in solution. This is also to be understood as meaning complexes of the active compound with other molecules and ions, in particular complexes which are complexed via ionic interactions. In particular, this is understood as meaning (and this is also a preferred embodiment of this invention) physiologically acceptable salts, in particular physiologically acceptable salts with cations or bases and physiologically acceptable salts with anions or acids or also a salt formed with a physiologically acceptable acid or a physiologically acceptable cation.

The preferred salt of the compounds used is the hydrochloride.

Physiologically acceptable is to be understood as meaning that the substance, in particular the salt as such, is acceptable when used on humans or mammals, that is to say, for example, does not have a non-physiological (e.g. toxic) action.

In the context of this invention, the term physiologically acceptable salt with anions or acids is understood as meaning salts of at least one of the compounds according to the invention—usually protonated, for example on the nitrogen—as the cation with at least one anion which is physiologically acceptable—in particular when used on humans and/or mammals. In particular, in the context of this invention this is understood as meaning the salt formed with a physiologically acceptable acid, namely salts of the particular active compound with inorganic or organic acids which are physiologically acceptable—in particular when used on humans and/or mammals. Examples of physiologically acceptable salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid, citric acid, glutamic acid, 1,1-dioxo-1,2-dihydro-1$\lambda^6$-benzo[d]isothiazol-3-one (saccharin), monomethylsebacic acid, 5-oxoproline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid. The hydrochloride salt is particularly preferred.

In the context of this invention, the term salt formed with a physiologically acceptable acid is understood as meaning salts of the particular active compound with inorganic or organic acids which are physiologically acceptable—in particular when used on humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydro-1$\lambda^6$-benzo[d]isothiazol-3-one (saccharin), monomethylsebacic acid, 5-oxoproline, hexane-1-sulfonic acid, nicotinic acid, 2-, 3- or 4-aminobenzoic acid, 2,4,6-trimethylbenzoic acid, α-liponic acid, acetylglycine, acetylsalicylic acid, hippuric acid and/or aspartic acid.

In the context of this invention, the term physiologically acceptable salt with cations or bases is understood as meaning at least one of the compounds according to the invention—usually a (deprotonated) acid—as the anion with at least one, preferably inorganic cation, which are physiologically acceptable—in particular when used on humans and/or mammals. Particularly preferred salts are the salts of the alkali metals and alkaline earth metals, but also with $NH_4^+$, in particular (mono)- or (di)sodium, (mono)- or (di)potassium, magnesium or calcium salts.

In the context of this invention, the term salt formed with a physiologically acceptable cation is understood as meaning salts of at least one of the particular compounds as the anion with at least one inorganic cation which is physiologically acceptable—in particular when used on humans and/or mammals. Particularly preferred salts are the salts of the alkali metals and alkaline earth metals, but also $NH_4^+$, in particular (mono)- or (di)sodium, (mono)- or (di)potassium, magnesium or calcium salts.

The present invention also provides a method for treatment of anxiety disorders in a mammal and/or human, in which a therapeutically active amount of a compound used according to the invention is administered.

In this context, it is of advantage to administer this compound at the first occurrence of anxiety disorders, since they show an early onset of action.

The present invention also provides a method for treatment of anxiety disorders or depressions, in which a compound used according to the invention is administered as an adjuvant to standard antidepressants, in order to inhibit the psychomotor states of excitation induced by the antidepressants at the start of therapy and the increased risk of suicide. In the context of this invention, standard antidepressants are understood as meaning all the approved antidepressants.

According to the present investigations, the substances used, and in particular (1R,2R)-3-(2-diethylaminomethyl-cyclohexyl)-phenol, are potent anxiolytics, antidepressants and analgesics, that is to say have an additional and clinically relevant anxiolytic action component.

The compounds used according to the invention can moreover also be employed for the preparation of a pharmaceutical formulation for treatment of obsessive compulsive disorders, migraine, fibromyalgia, eating disorders, bulimia, hyperactivity, drug dependency, addiction and withdrawal, trichotillomania, Tourette's syndrome, skin diseases, in particular postherapeutic neuralgia and pruritus, psychoses, impaired memory, cognitive disorders and/or Alzheimer's disease.

Suitable additives and/or auxiliary substances to the compounds used according to the invention in the process for the preparation of the pharmaceutical formulation are all the substances known to the expert from the prior art for achieving galenical formulations. The choice of these auxiliary substances and the amounts thereof to be employed depend on whether the pharmaceutical formulation is to be administered orally, intravenously, intraperitoneally, intradermally, intramuscularly, intranasally, buccally or locally. Formulations in the form of tablets, chewable tablets, coated tablets, capsules, granules, drops, juices or syrups are suitable for oral administration, and solutions, suspensions, easily reconstitutable dry formulations and sprays are suitable for parenteral, topical and inhalatory administration. Suppositories for use in the rectum are a further possibility. The use in a depot in dissolved form, a carrier film or a patch, optionally with the addition of agents which promote penetration through the skin, are examples of suitable forms for percutaneous administration. Examples of auxiliary substances and additives for the oral administration forms are disintegrating agents, lubricants, binders, fillers, mould release agents, optionally solvents, flavourings, sugars, in particular carrier agents, diluents, dyestuffs, antioxidants etc. For suppositories, inter alia, waxes and fatty acid esters can be used, and for parenteral administration compositions carrier substances, preservatives, suspension auxiliaries etc. can be used. The amounts of active compound to be administered to patients vary as a function of the weight of the patient, the mode of administration and the severity of the disease. The compounds used according to the invention can be released in a delayed manner from formulation forms which can be used orally, rectally or percutaneously. Corresponding sustained-release formulations, in particular in the form of a "once daily" preparation which has to be taken only once a day, are particularly preferred for the indication according to the invention.

Pharmaceutical formulations which comprise at least 0.05 to 90.0% of the active compound, in particular low active dosages, in order to avoid side effects or analgesic actions, are preferred. 0.1 to 5,000 mg/kg, in particular 1 to 500 mg/kg, preferably 2 to 250 mg/kg of body weight of a least one compound used according to the invention are conventionally administered. However, the administration of 0.01-5 mg/kg, preferably 0.03 to 2 mg/kg, in particular 0.05 to 1 mg/kg, is also preferred and conventional.

Auxiliary substances can be, for example: water, ethanol, 2-propanol, glycerol, ethylene glycol, propylene glycol, polyethylene glycol, polypropylene glycol, glucose, fructose, lactose, sucrose, dextrose, molasses, starch, modified starch, gelatine, sorbitol, inositol, mannitol, microcrystalline cellulose, methylcellulose, carboxymethylcellulose, cellulose acetate, shellac, cetyl alcohol, polyvinylpyrrolidone, paraffins, waxes, naturally occurring and synthetic gums, gum acacia, alginates, dextran, saturated and unsaturated fatty acids, stearic acid, magnesium stearate, zinc stearate, glyceryl stearate, sodium lauryl sulfate, edible oils, sesame oil, coconut oil, groundnut oil, soya bean oil, lecithin, sodium lactate, polyoxyethylene and -propylene fatty acid esters, sorbitan fatty acid esters, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulfate, zinc sulfate, calcium sulfate, potash, calcium phosphate, dicalcium phosphate, potassium bromide, potassium iodide, talc, kaolin, pectin, crospovidone, agar and bentonite.

The pharmaceutical formulations and pharmaceutical compositions are prepared with the aid of means, devices, methods and processes which are well-known in the prior art of pharmaceutical formulation, such as are described, for example, in "Remington's Pharmaceutical Sciences", ed. A. R. Gennaro, 17th ed., Mack Publishing Company, Easton, Pa. (1985), in particular in part 8, chapter 76 to 93.

Thus e.g. for a solid formulation, such as a tablet, the active compound of the pharmaceutical formulation, i.e. a compound of [2-(3-methoxyphenyl)-cyclohexylmethyl]-dimethylamine, its metabolites or one of the pharmaceutically acceptable salts, can be granulated with a pharmaceutical carrier, e.g. conventional tablet constituents, such as maize starch, lactose, sucrose, sorbitol, talc, magnesium stearate, dicalcium phosphate or pharmaceutically acceptable gums, and pharmaceutical diluents, such as e.g. water, in order to form a solid composition which comprises a compound according to the invention or a pharmaceutically acceptable salt thereof in homogeneous distribution. Homogeneous distribution is understood here as meaning that the active compound is uniformly distributed over the entire composition, so that this can easily be divided into unit dose forms, such as tablets, pills or capsules, having the same activity. The solid composition is then divided into unit dose forms. The tablets or pills of the pharmaceutical formulation according to the invention or of the compositions according to the invention can also be coated or compounded in another manner in order to provide a dose form with delayed release. Suitable coating compositions are, inter alia, polymeric acids and mixtures of polymeric acids with materials such as e.g. shellac, cetyl alcohol and/or cellulose acetate.

Although the pharmaceutical formulations show only few side effects, it may be of advantage—should this be necessary at all—for example to avoid certain forms of dependency, also to use morphine antagonists, in particular naloxone, naltrexone and/or levallorphan, in addition to the compounds used.

[2-(3-Methoxyphenyl)-cyclohexylmethyl]-dimethylamine and (1R,2R)-[2-(3-methoxyphenyl)-cyclohexylmethyl]-dimethylamine and their preparation are known from DE 195 25 137 A1 example 8 and U.S. Pat. No. 5,733,936 example 8, where the absolute stereochemistry of the compound (−6) prepared according to example 8 is certainly correctly (1R,2R) and not (1R,2S). 3-(2-Dimethylaminomethyl-cyclohexyl)-phenol and (1R,2R)-3-(2-dimethylaminomethyl-cyclohexyl)-phenol and their preparation are also known from DE 195 25 137 A1 example 10 and U.S. Pat. No. 5,733,936 example 10, where the absolute stereochemistry of the compound (−7) prepared according to example 10 is certainly correctly (1R,2R) and not (1R,2S).

The compounds and their preparation which are not yet known from DE 195 25 137 A1 or U.S. Pat. No. 5,733,936 were prepared in accordance with the examples.

Certain embodiments of the present invention may be further understood by reference to the following specific examples. These examples and the terminology used herein are for the purpose of describing particular embodiments only and are not intended to be limiting.

EXAMPLES

Generally, the purification and enantiomer separation in all the processes mentioned as an example are carried out at the various stages by column chromatography or, predominantly, HPLC, where appropriate on chiral stationary phases.

Example 1

Preparation of (1R,2R)-[2-(3-methoxyphenyl)-cyclohexylmethyl]-methylamine hydrochloride

[2-(3-Methoxyphenyl)-cyclohexylmethyl]-methylamine and (1R,2R)-[2-(3-methoxyphenyl)-cyclohexylmethyl]-methylamine, in particular the hydrochloride salt thereof, are prepared as follows:

3.16 ml (25.2 mmol) phenyl chloroformate were added dropwise to a solution of 5.67 g (22.9 mmol) (1R,2R)-[2-(3-methoxyphenyl)-cyclohexylmethyl]-dimethylamine in 390 ml dry toluene at the boiling point. After the mixture had been heated under reflux for three hours, it was cooled to 20° C., and washed successively with 100 ml each of sodium hydroxide solution (2.5N), distilled water, hydrochloric acid (1N) and a saturated sodium chloride solution. It was dried over sodium sulfate and evaporated in vacuo. The residue was taken up in 192.5 ml ethylene glycol and 46 ml sodium hydroxide solution (5N) and the mixture was stirred at 110° C. for a total of 8 hours, it being topped up twice with 10 ml sodium hydroxide solution (5N) each time. After cooling, it was diluted with 100 ml distilled water and extracted three times with 50 ml methylene chloride each time. The extracts were washed with distilled water and a saturated sodium chloride solution, dried over sodium sulfate and evaporated in vacuo and the residue was dried. The residue (5.03 g) was dissolved in 32.3 ml 2-butanone, 2.7 ml trimethylchlorosilane were added to the solution and the mixture was stirred for 15 minutes. 100 ml dry diethyl ether were then added, the mixture was stirred at 20° C. for a further 2 hours and the solid was filtered off with suction. It was washed thoroughly with diethyl ether and dried in vacuo. By this procedure, 3.56 g (57.6% of theory) of the title compound were obtained in the form of colourless crystals which melted at 165-167° C.

Example 2

Preparation of (1R,2R)-3-(2-methylaminomethyl-cyclohexyl)-phenol hydrochloride 3.55 g (15.2 mmol) of the product from example 1 were stirred under reflux in 4.59 ml hydrobromic acid (47-48% HBr) for 7.5 h. After cooling, ice/water was added and the mixture was then rendered alkaline with sodium hydroxide solution (6N). It was extracted three times with 50 ml ethyl acetate each time. The extracts were washed with a saturated sodium chloride solution, dried over sodium sulfate and evaporated in vacuo. The residue (2.91 g) was dissolved in 16.4 ml 2-butanone and converted into the hydrochloride with 1.63 ml trimethylchlorosilane as described under example 1. By this procedure, 2.98 g (76.5% of theory) of the title compound were obtained as a slightly yellow-coloured solid which melted at 173-175° C.

Example 3

Preparation of sulfuric acid mono-(1R,2R)-[3-(2-dimethylaminomethyl-cyclohexyl)-phenyl]ester Sulfuric acid mono-[3-(2-dimethylaminomethyl-cyclohexyl)-phenyl]ester or sulfuric acid mono-(1R,2R)-[3-(2-dimethylaminomethyl-cyclohexyl)-phenyl]ester was prepared as follows:

15.9 g (4.70 mmol) of a 2.9% strength solution of sulfuric acid in dimethylformamide were added dropwise to a solution of 1.00 g (3.92 mmol) (1R,2R)-3-(2-dimethylaminomethyl-cyclohexyl)-phenol; hydrochloride and 0.94 g (4.70 mmol) dicyclohexylcarbodiimide in 20 ml dimethylformamide at 0° C., while stirring. When the addition had ended, the mixture was stirred further for another 10 minutes and a pH of 9 was then established with dilute ammonium hydroxide solution. The precipitate formed was separated off, washed with ethyl acetate and dried in vacuo. 0.26 g (21% of theory) of the title compound was obtained in this way as a white solid.

Example 4

Preparation of 6-[(1R,2R)-3-(2-dimethylaminomethyl-cyclohexyl)-phenoxy]-3,4,5-trihydroxy-tetrahydropyran-2-carboxylic acid 6-[3-(2-Dimethylaminomethyl-cyclohexyl)-phenoxy]-3,4,5-trihydroxy-tetrahydropyran-2-carboxylic acid and 6-[(1R,2R)-3-(2-Dimethylaminomethyl-cyclohexyl)-phenoxy]-3,4,5-trihydroxy-tetrahydropyran-2-carboxylic acid were prepared as follows:

A mixture of 2.33 g (10 mmol) (1R,2R)-3-(2-dimethylaminomethyl-cyclohexyl)-phenol, 3.58 g (9 mmol) acetobromo-α-D-glucuronic acid methyl ester and 0.23 g (9.5 mmol) lithium hydroxide in 23 ml dry methanol was first stirred at 20° C. for 30 minutes, a solution of 0.65 g lithium hydroxide in 25 ml water was then added and the mixture was stirred again for 30 minutes. It was extracted with ethyl acetate and the aqueous phase was adjusted to a pH of 3.5 by addition of acetic acid and extracted again with ethyl acetate. The aqueous phase was evaporated in vacuo and the residue was purified by HPLC. 0.85 g (23% of theory) of the title compound was obtained in this manner in the form of a white powder.

Example 5

Preparation of (1R,2R)-3-(2-dimethylaminomethyl-cyclohexyl)-phenol, N-oxide 3-(2-Dimethylaminomethyl-cyclohexyl)-phenol, N-oxide and (1R,2R)-3-(2-dimethylaminomethyl-cyclohexyl)-phenol, N-oxide were prepared as follows:

10.5 ml hydrogen peroxide were added to a solution of 5.60 g (24 mmol) (1R,2R)-3-(2-dimethylaminomethyl-cyclohexyl)-phenol in 28 ml methanol and the mixture was stirred first at 50° C. for 3 hours and then at 20° C. for 15 hours. After addition of 3.30 g potassium carbonate, the mixture was stirred again for 3 hours, the solid was then filtered off and the filtrate was evaporated in vacuo. The residue was taken up in 30 ml ethanol. Solid constituents were separated off by filtration, the filtrate was evaporated in vacuo and the residue was dried. 5.50 g (80% of theory) of the title compound were obtained in this way in the form of an oil which gradually solidified.

Example 6

Preparation of [2-(3-methoxy-phenyl)-cyclohexylmethyl]-dimethylamine, N-oxide

[2-(3-Methoxy-phenyl)-cyclohexylmethyl]-dimethylamine, N-oxide and (1R,2R)-[2-(3-methoxy-phenyl)-cyclohexylmethyl]-dimethylamine, N-oxide were prepared by the procedure in example 5 using corresponding starting substances.

Example 7

Preparation of 4-(2-dimethylaminomethyl-cyclohexyl)-catechol

The preparation of 4-(2-dimethylaminomethyl-cyclohexyl)-catechol was carried out in accordance with the following reaction equation (stereochemistry not taken into consideration):

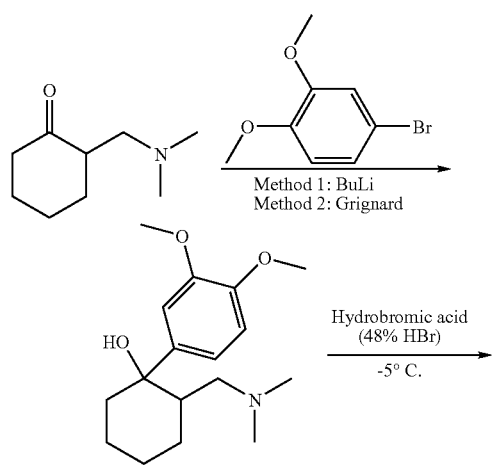

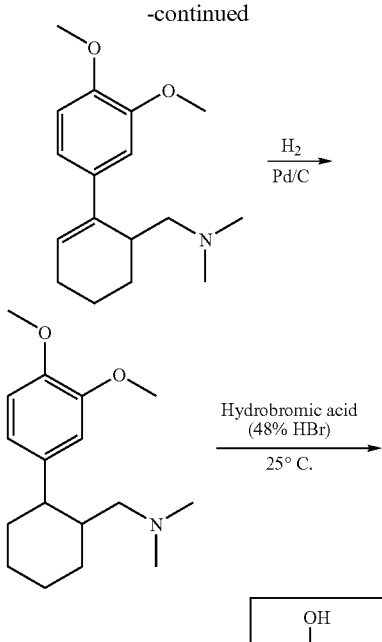

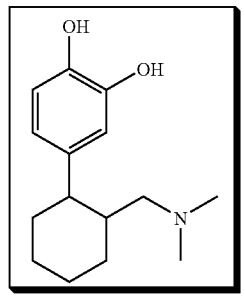

In this equation, Method 1 BuLi moreover means the synthesis, well-known to the expert, via bromine-lithium exchange with BuLi reagents and Method 2 Grignard means the synthesis, well-known to the expert, via Mg reagents.

Example 8

Preparation of C-[2-(3-methoxy-phenyl)-cyclohexyl]-methylamine

The preparation of C-[2-(3-methoxy-phenyl)-cyclohexyl]-methylamine was carried out in accordance with the following reaction equation (stereochemistry not taken into consideration; Bn represents the benzyl radical):

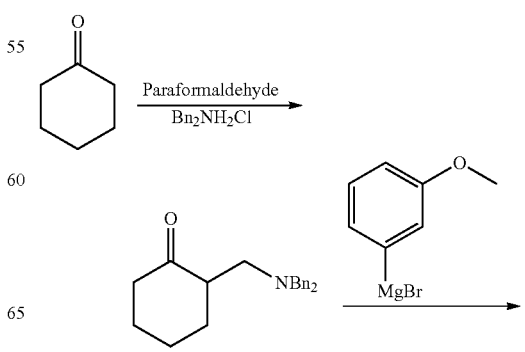

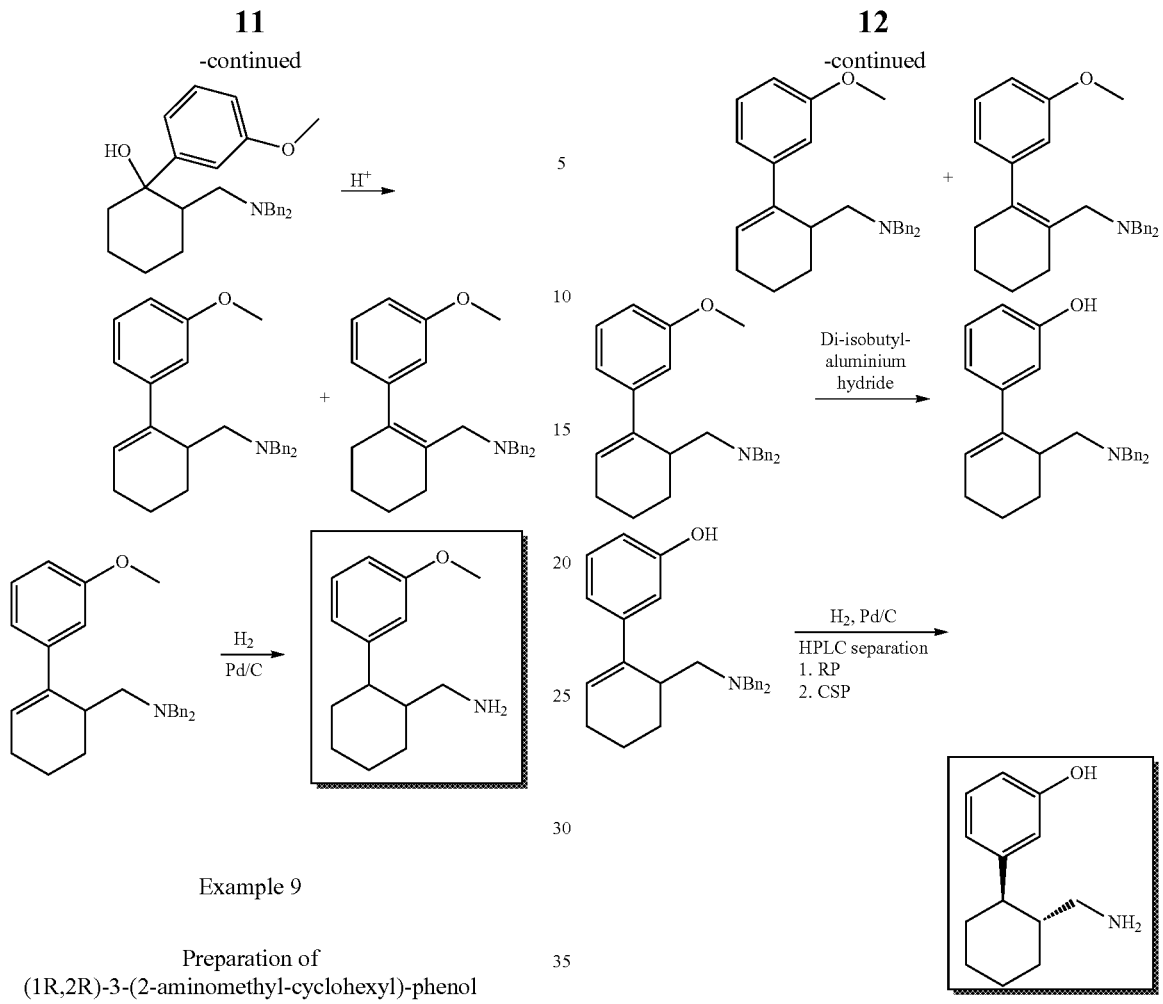

Example 9

Preparation of (1R,2R)-3-(2-aminomethyl-cyclohexyl)-phenol

The preparation of 3-(2-aminomethyl-cyclohexyl)-phenol or (1R,2R)-3-(2-aminomethyl-cyclohexyl)-phenol was carried out in accordance with the following reaction equation:

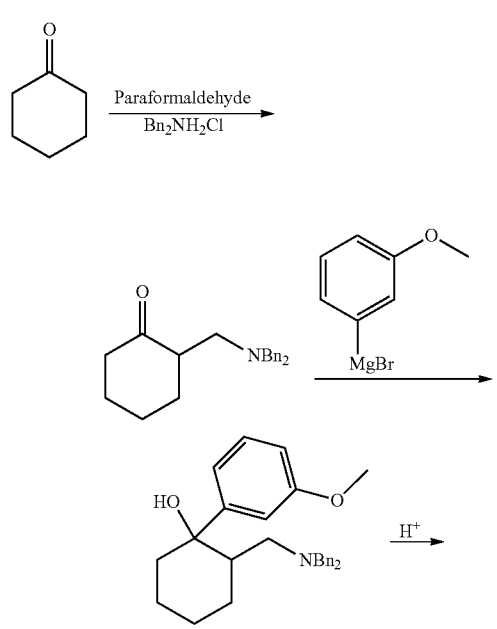

RP = Reversed Phase
CSP = Chiral Stationary Phase

Example 10

In Vitro Isolation of the Metabolites

[2-(3-Methoxyphenyl)-cyclohexylmethyl]-dimethylamine hydrochloride and in another example (1R,2R)-3-(2-dimethylaminomethyl-cyclohexyl)-phenol hydrochloride was dissolved in TRIS/HCl buffer pH 7.4. MgCl and, where appropriate, the other necessary cofactors for cytochrome P450 (CytP450) known from the literature were then added and the mixture was incubated with CytP450 3A4 (N-demethylation) and/or CytP450 2D6 (O-demethylation) at 37° C. The batch was subsequently separated via HPLC and the metabolites in the fractions were identified via NMR and then isolated from the fractions.

Example 11

In Vivo Isolation of the Metabolites

A mammal was injected with [2-(3-methoxyphenyl)-cyclohexylmethyl]-dimethylamine hydrochloride and in a further example (1R,2R)-3-(2-dimethylaminomethyl-cyclohexyl)-phenol hydrochloride. Blood was taken from the mammal and, after separating off corpuscular constituents, was separated via HPLC and the metabolites in the fractions were identified via NMR and then isolated from the fractions.

Example 12

Parenteral Administration Form 1 g (1R,2R)-3-(2-dimethylaminomethyl-cyclohexyl)-phenol hydrochloride is dissolved in 1 l water for injection purposes at room temperature and the solution is then adjusted to isotonic conditions by addition of NaCl.

Pharmacological Studies a) Methods for Determination of the Affinity for the Human μ-Opiate Receptor and the 5-HT and NA Reuptake Inhibition Investigation of the affinity for the human μ-opiate receptor The receptor affinity for the human μ-opiate receptor is determined in a homogeneous set-up in microtitre plates. For this, dilution series of the substances to be tested are incubated with a receptor membrane preparation (15-40 μg protein/250 μl incubation batch) of CHO-K1 cells which express the human μ-opiate receptor (RB-HOM receptor membrane preparation from Perkin Elmer, Zaventem, Belgium) in the presence of 1 nmol/l of the radioactive ligand [$^3$H]-naloxone (NET719, Perkin Elmer, Zaventem, Belgium) and 1 mg WGA-SPA-Beads (wheat germ agglutinin SPA beads from Amersham/Pharmacia, Freiburg, Germany) in a total volume of 250 μl for 90 minutes at room temperature. 50 mmol/l Tris-HCl supplemented with 0.05% sodium azide and with 0.06% bovine serum albumin is used as the incubation buffer. 25 μmol/l naloxone are additionally added for determination of the non-specific binding. After the end of the ninety-minute incubation time, the microtitre plates are centrifuged for 20 minutes at 1,000 g and the radioactivity is measured in a μ-counter (Microbeta-Trilux, PerkinElmer Wallac, Freiburg, Germany). The percentage displacement of the radioactive ligand from its binding to the human μ-opiate receptor is determined at a concentration of the test substances of 1 μmol/l and stated as the percentage inhibition of the specific binding. Starting from the percentage displacement by various concentrations of the test substances, $IC_{50}$ inhibitory concentrations which cause a 50 percent displacement of the radioactive ligand are calculated. By conversion by means of the Cheng-Prusoff relationship, $K_i$ values for the test substances are obtained (Cheng and Prusoff 1973).

Investigations of the 5-HT and NA Reuptake Inhibition

In order to be able to carry out these in vitro studies, synaptosomes are freshly isolated from areas of the rat brain. (In each case N=4, i.e. means±SEM from 4 independent series of experiments, which were carried out in triplicate parallel studies).

A detailed description of the method is contained in the publication of Frink, Hennies, Englberger et al. (1996) (the study can also be conducted on microtitre plates (250 μl/well) at room temperature).

Evaluations:

In addition to % inhibitions at fixed test substance concentrations (e.g. $1\times10^{-6}$ M or $1\times10^{-5}$ M in the batch), dose dependencies were investigated. $IC_{50}$ values are obtained by this means, and can be converted into inhibitor constants ($K_i$) in accordance with the "Cheng-Prusoff equation" (Cheng and Prusoff 1973). The $IC_{50}$ values were obtained with the aid of the computer program "Figure P" (version 6.0, Biosoft, Cambridge, England). Km values were calculated in accordance with the method of Lineweaver and Burk (1934). The computer program "Ligand" (version 4, Biosoft, England) was used to display $K_D$ values.

LITERATURE

Frink; M. Ch., Hennies, H.-H., Englberger, W., Haurand, M. and Wilffert B. (1996) Arzneim.-Forsch./Drug Res. 46 (III), 11, 1029-1036

Gray, E. G. and Whittaker V. P. (1962) J. Anat. 76, 79-88

Cheng, Y. C. and Prusoff, W. H. (1973) Biochem. Pharmacol. 22, 3099-3108

Lineweaver, H. and Burk, D. (1934) J. Am. Chem. Soc. 56, 658-666

A clear affinity for the μ-opiate receptor and an inhibition of serotonin or noradrenaline reuptake were measured for the compounds according to the invention. For the compound 3-(2-dimethylaminomethyl-cyclohexyl)-phenol in particular a balanced ratio between the μ-opioid component and the monoamine reuptake inhibition was found, the latter being in the order of magnitude of substances used clinically. The compound 3-(2-dimethylaminomethyl-cyclohexyl)-phenol therefore has a very promising potential for use as an anxiolytic, antidepressant and analgesic.

The results of examples and for the reference substance venlafaxine are shown in the following table.

TABLE 1

| Compound | μ-Opioid receptor affinity (Ki values (μmol/l) | 5-HT reuptake inhibition (Ki values, μmol/l) | NA reuptake inhibition (Ki values, μmol/l) |
|---|---|---|---|
| 3-(2-Dimethylaminomethyl-cyclohexyl)-phenol, hydrochloride | 0.14 | 0.05 | 0.16 |
| 3-(2-Methylaminomethyl-cyclohexyl)-phenol hydrochloride | 0.87 | 5.67 | 0.48 |
| Venlafaxine | inactive | 0.062 | 0.45 |

In each case a so-called "$P_2$" fraction, which is prepared exactly in accordance with the instructions of Gray and Whittaker (1962), is used. For the NA reuptake these vesicular particles are isolated from the hypothalamus, and for the 5-HT reuptake from the medulla+pons region of male rat brains.

The following characteristic data were determined for the NA and 5-HT reuptake:

NA uptake: Km=0.32±0.11 μM

5-HT uptake: Km=0.084±0.011 μM b) Investigation of the Onset of Anxiolytic Actions in the Elevated Plus Maze Test on Rats In the elevated plus maze test the actions of substances on the endogenous anxiety of rodents towards open and elevated places are determined.

The apparatus was placed approx. 1 m above the floor and comprised four arms arranged in a cross, two opposite arms being open and two closed. The rats were placed individually in the central square compartment, from where access to all four arms was possible, and the behaviour of the animals was observed for 5 minutes. The duration of stay and the number of entries into the open arms were evaluated. The group size was 10-15 animals. The single administration of the test substances or of the control vehicle took place 30 min before testing.

It is reported in the literature that benzodiazepines induce an increased duration of stay and entries into the open compartment. In contrast, antidepressants of which the main mechanism is inhibition of reuptake of the monoamines serotonin and/or noradrenaline cause no anxiolytic action, but in some cases anxiogenic effects, after a single administration in the elevated plus maze test, and anxiolytic effects can be observed only after chronic administration over 2-4 weeks (Borsini, F., Podhorna, J., Marazziti, D., Psychopharmacology, 2002, 163, p. 121-141). The typical disadvantages of monoamine reuptake inhibitors in the therapy of anxiety patients, namely the delayed onset of action and the initially anxiogenic-like effects, can thus be followed in the elevated plus maze test on rats. The elevated plus maze test is therefore a suitable animal model for the investigation of new therapies which have the aim of accelerating the onset of action of monoamine reuptake inhibitors.

After a single administration of the compound 3-(2-dimethylaminomethyl-cyclohexyl)-phenol, a significant increase in the duration of stay and a clear increase in the number of entries into the open arms and therefore significant anxiolytic actions were measured. In no case was an anxiogenic-like action induced after acute administration of the example of 3-(2-dimethylaminomethyl-cyclohexyl)-phenol. When 3-(2-dimethylaminomethyl-cyclohexyl)-phenol was combined with the μ-opiate receptor antagonist naloxone, the anxiolytic effects of 3-(2-dimethylaminomethyl-cyclohexyl)-phenol could thereby be eliminated completely. The naloxone sensitivity of the anxiolytic effects of 3-(2-dimethylaminomethyl-cyclohexyl)-phenol demonstrate that the opiate component of 3-(2-dimethylaminomethyl-cyclohexyl)-phenol is decisive for the early onset of action after a single administration of the substance.

Diazepam caused an increase in the duration of stay and the entries into the open arms. The mixed serotonin and noradrenaline reuptake inhibitor venlafaxine showed no anxiolytic action after a single administration.

The results for 3-(2-dimethylaminomethyl-cyclohexyl)-phenol and for the reference substances diazepam and venlafaxine are shown in the following table.

TABLE 2

| Substance | Dose (mg/kg i.p.) | Open arms Duration of stay (sec) | Number of entries |
|---|---|---|---|
| Vehicle | — | 16.8 | 2.2 |
| 3-(2-Dimethylamino-methyl-cyclohexyl)-phenol | 8 | 29.0 | 3.2 |
|  | 16 | 118.2* | 8.5 |
| 3-(2-Dimethylamino-methyl-cyclohexyl)-phenol + naloxone | 16 + 1 | 37.1# | 1.6 |
| Naloxone | 1 | 28.6 | 4.5 |
| Diazepam | 2 | 77.7* | 8.1* |
| Vehicle | — | 41.6 | 4.3 |
| Venlafaxine | 16 | 66.9 | 4.6 |

Statistical evaluation: Anova plus post-hoc Dunnett's test (Significance level: $p<0.05$; *: significant versus vehicle; #: significant versus intrinsic effect of 16 mg/kg i.p. 3-(2-dimethylaminomethyl-cyclohexyl)-phenol).

The foregoing description and examples have been set forth merely to illustrate the invention and are not intended to be limiting. Since modifications of the described embodiments incorporating the spirit and substance of the invention may occur to person skilled in the art, the invention should be construed broadly to include all variations within the scope of the appended claims and equivalents thereof.

The invention claimed is:

1. A method of treating fibromyalgia or chronic pain due to fibromyalgia in a subject, said method comprising administering to said subject a pharmacologically effective amount of a compound selected from the group consisting of:
   3-(2-dimethylaminomethyl-cyclohexyl)-phenol,
   (1R,2R)-3-(2-dimethylaminomethyl-cyclohexyl)-phenol,
   and physiologically acceptable salts thereof.

2. A method according to claim 1, wherein said compound is administered in the form of a pharmaceutical composition further comprising at least one pharmaceutically acceptable carrier or adjuvant.

3. A method according to claim 1, wherein said compound is present in the form of a free base.

4. A method according to claim 1, wherein said compound is present in the form of an isolated stereoisomer.

5. A method according to claim 4, wherein said compound is present in the form of a 1R,2R enantiomer.

6. A method according to claim 1, wherein said compound is present in the form of a mixture of stereoisomers in any mixing ratio.

7. A method according to claim 6, wherein said compound is present in the form of a racemic mixture.

8. A method according to claim 1, wherein said compound is present in the form of a physiologically acceptable salt.

9. A method according to claim 8, wherein said physiologically acceptable salt is a hydrochloride salt.

* * * * *